United States Patent
Teitz et al.

(10) Patent No.: US 12,053,446 B1
(45) Date of Patent: *Aug. 6, 2024

(54) METHODS FOR THE PREVENTION AND TREATMENT OF HEARING LOSS USING OSELTAMIVIR

(71) Applicant: Ting Therapeutics LLC, Omaha, NE (US)

(72) Inventors: Tal Teitz, Omaha, NE (US); Jian Zuo, Omaha, NE (US); Taosheng Chen, Germantown, TN (US)

(73) Assignees: Ting Therapeutics LLC, Omaha, NE (US); St Jude Children's Research Hospital, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/129,267

(22) Filed: Mar. 31, 2023

Related U.S. Application Data (63) Continuation of application No. 18/106,918, filed on Feb. 7, 2023.

(60) Provisional application No. 63/311,849, filed on Feb. 18, 2022.

(51) Int. Cl.
| | | |
|---|---|---|
| *A61K 31/196* | (2006.01) | |
| *A61K 31/282* | (2006.01) | |
| *A61K 31/7028* | (2006.01) | |
| *A61P 27/16* | (2006.01) | |

(52) U.S. Cl.
CPC .......... *A61K 31/196* (2013.01); *A61K 31/282* (2013.01); *A61K 31/7028* (2013.01); *A61P 27/16* (2018.01)

(58) Field of Classification Search
None
See application file for complete search history.

(56) References Cited

FOREIGN PATENT DOCUMENTS

WO    WO-2013063679 A1 *  5/2013  ........... A61K 31/138

OTHER PUBLICATIONS

NIH National Cancer Institute (NCI). Sodium Thiosulfate Prevents Cisplatin-Induced Hearing Loss in Some Children. Published Jul. 2018. Retrieved from the internet on Jan. 2, 2024, https://www.cancer.gov/news-events/cancer-currents-blog/2018/cisplatin-hearing-loss-sodium-thiosulfate. (Year: 2018).*
Takahashi, N., Abe, R., Hattori, N. et al. Clinical course of a critically ill patient with severe acute respiratory syndrome coronavirus 2 (SARS-CoV-2). J Artif Organs 23, 397-400 (2020). (Year: 2020).*
Blum. Acute unilateral sensorineural hearing loss due to H1N1 infection. The Israel Medical Association Journal. Published Jul. 2010. (Year: 2010).*
CDC. Preventing Noise Induced Hearing Loss. Retrieved from the WayBack Machine on Jan. 22, 2024, https://web.archive.org/web/20211215084012/https://www.cdc.gov/ncbddd/hearingloss/noise.html. Published Dec. 15, 2021. (Year: 2021).*
Narozny et al. In Reference to the Challenges of Pharmacotherapy of SARA-CoV-2 Infection in Patients with Sudden Sensorineural Hearing Loss Due to Covid-19. The American Laryngological, Rhinological and Otological Society. Published 2021. (Year: 2021).*
Rybak et al. Frontiers in Cellular Neuroscience. Local Drug Delivery for Prevention of Hearing Loss. Published Jul. 9, 2019. (Year: 2019).*
Henderson, Emily. Repurposed drug can treat hearing loss in humans. Retrieved from the Internet on Jan. 22, 2024, https://www.news-medical.net/news/20210107/Repurposed-drug-can-treat-hearing-loss-in-humans.aspx. Published on Jan. 7, 2021. (Year: 2021).*
Mukherjea D, Rybak LP, Sheehan KE, Kaur T, Ramkumar V, Jajoo S, Sheth S. The design and screening of drugs to prevent acquired sensorineural hearing loss. Expert Opin Drug Discov. May 2011;6(5):491-505. (Year: 2011).*
Lamounier P, Franco Gonçalves V, Ramos HVL, Gobbo DA, Teixeira RP, Dos Reis PC, Bahmad F Jr, Cândido Costa C. A 67-Year-Old Woman with Sudden Hearing Loss Associated with SARS-CoV-2 Infection. Am J Case Rep. Nov. 3, 2020;21:e927519. (Year: 2020).*
PubChem. Oseltamivir. Retrieved from the Internet on Jan. 22, 2024, https://pubchem.ncbi.nlm.nih.gov/compound/65028 (Year: 2024).*
M. Ingersoll, R. Lutze, T Teitz, D. Kresock, D. Currier, T. Chen, J. Zuo; Tamiflu as a Therapeutic Candidate for Noise-Induced Hearing Loss, Feb. 5, 2022, 416-416, The Association for Research in Otolaryngology, Orlando, FL.

* cited by examiner

*Primary Examiner* — Amy C Bonaparte
*Assistant Examiner* — Lauren Wells
(74) *Attorney, Agent, or Firm* — Veritay Group IP PLLC; Susan Fentress (57) ABSTRACT

Oseltamivir is used as active agent to treat a hearing impairment and to prevent a hearing impairment, and a method of treating and/or preventing hearing impairments or disorders using Oseltamivir are disclosed. Oseltamivir exhibits excellent protection against noise-induced hearing loss and against cisplatin-induced hearing loss.

4 Claims, 14 Drawing Sheets

METHODS FOR THE PREVENTION AND TREATMENT OF HEARING LOSS USING OSELTAMIVIR

CROSS-REFERENCE TO RELATED APPLICATIONS

This application is a continuation of patent application of U.S. Ser. No. 18/106,918 filed Feb. 7, 2023 and, claims the benefit of U.S. provisional patent application Ser. No. 63/311,849 filed Feb. 18, 2022, hereby incorporated by reference.

Statement regarding federally sponsored research or development: This research was funded by the following grants to T. Teitz; DoD W81XWH-21-1-0696, RH200032, LB 506 Nebraska state, Cancer and Smoking Disease Research Program, LB 692 Nebraska Biomedical Research Development Fund. The government has certain rights in the invention.

FIELD OF THE INVENTION

The present invention relates to therapeutic uses of active agents such as for treating, inhibiting, and/or preventing hearing loss.

DESCRIPTION OF RELATED ART INCLUDING INFORMATION DISCLOSED UNDER 37 CFR 1.97 AND 37 CFR 1.98

Over 35 million Americans suffer from hearing impairment. In mammals, hair cell impairment is permanent. Acquired hearing loss due to chemotherapy or noise exposure is a major health problem and Cisplatin chemotherapy often causes permanent hearing loss in cancer patients. However, there are no FDA-approved drugs for the treatment or prevention of Cisplatin- or noise-induced hearing loss. Platinum-based chemotherapy is a standard of care for various types of cancers, including ovarian, lung, testicular, and head and neck carcinoma. Cisplatin, one of the most effective platinum compounds, causes permanent hearing loss in 40-60% of treated cancer patients. Nearly half of people over the age of 75 years suffer from age-related hearing loss, the cause of which has been considered to be accumulated noise exposure and other ototoxic insults over life time. A major cause of hearing impairment due to ototoxic insults, such as antibiotics, chemotherapeutic drugs, noise or aging is cell death in the inner ear. One of the known mechanisms of Cisplatin damage to the auditory sensory cells is DNA adduct formation leading to oxidative stress and cellular apoptosis.

The spiral-shaped cochlea of the inner ear is responsible for detecting sound. Inner hair cells lining the cochlea transform the mechanical vibrations of sound waves into chemical signals. These chemicals are then released from the hair cells and received by receptors on the auditory nerve fibers that send electrical impulses to the brain. The inner ear cells lining the cochlea can be destroyed by the use of antibiotics, chemotherapeutic drugs, noise or aging leading to a condition called sensorineural hearing impairment.

Currently, there are no clinically proven medications for the treatment of hearing impairment (sensorineural and neural), or tinnitus associated with the inner ear, and a medication that could be used to prevent, alleviate, or eliminate hearing impairment (or tinnitus) would thus be very desirable. The most common remedy for individuals suffering from severe sensorineural hearing impairment is a hearing aid, which functions to amplify sound. Hearing aids are non-invasive and can improve an individual's ability to hear. However, hearing aids can often be quite conspicuous and embarrassing to the wearer and hearing aids do not return hearing to normal levels. Furthermore, hearing aids amplify sound indiscriminately, sometimes amplifying sounds that an individual does not wish to hear, such as environmental noise. There exists a need in the art for a solution to hearing impairment due to noise, chemotherapeutic-treatment, and other ototoxic insults.

BRIEF SUMMARY OF THE INVENTION

The invention provides a method to prevent or treat hearing loss including the steps of administering to a subject in need thereof an effective amount of a pharmaceutical composition containing a therapeutically active agent, wherein the therapeutically active agent includes Oseltamivir. The subject can be a mammal such as a human or animal.

The invention provides a method to prevent or treat hearing loss including the steps of administering to an animal or human in need thereof an effective amount of a pharmaceutical composition containing a therapeutically active agent, wherein the therapeutically active agent includes: Oseltamivir, or a pharmaceutically acceptable salt thereof.

The inventive subject matter also includes a composition for use in preventing or treating hearing loss by protecting inner ear cells from death wherein the composition is an effective amount of an active agent, wherein the active agent includes: Oseltamivir or a pharmaceutically acceptable salt thereof.

The inventive subject matter also includes a kit made of an active agent, wherein the active agent includes: Oseltamivir or a pharmaceutically acceptable salt thereof; and one or more of: (A) at least one cancer drug or (B) instructions for preventing a hearing impairment.

BRIEF DESCRIPTION OF THE SEVERAL VIEWS OF THE DRAWING

The accompanying Figures, which are incorporated in and constitute a part of this specification, illustrate several aspects and together with the description serve to explain the principles of the invention.

DETAILED DESCRIPTION OF THE INVENTION

The present invention can be understood more readily by reference to the following detailed description of the invention and the examples included therein. Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

In one aspect, compounds can be used as a therapy for the treatment and/or prevention of hearing loss. In various aspects, the compounds and compositions of the invention can be administered in pharmaceutical compositions, which are formulated according to the intended method of administration. The compounds of this invention are defined as a therapeutically active agent in a treatment regimen or procedure that is intended for preventing hearing loss by noise or aging by protecting inner ear cells from death and in preventing hearing loss by chemotherapy or antibiotics induced hearing loss, Therapeutic agent means a chemical substance that is used for the treatment or mitigation of a disease condition or ailment.

In one aspect, compounds can be used as a therapy for the treatment and/or prevention of hearing loss. In various aspects, the compounds and compositions of the invention can be administered in pharmaceutical compositions, which are formulated according to the intended method of administration. The compounds of this invention are defined as a therapeutically active agent in a treatment regimen or procedure that is intended for preventing hearing loss by noise or aging by protecting inner ear cells from death and in preventing hearing loss by chemotherapy or antibiotics induced hearing loss. Therapeutic agent means a chemical substance that is used for the treatment or mitigation of a disease condition or ailment.

Unbiased high-throughput screens of 1,300 FDA-approved drugs for cisplatin-induced cell-death protection in an inner ear cell line HEI-OC1, and identified as one of the best hits, the drug oseltamivir phosphate (Oseltamivir, Oseltamivir). Oseltamivir is an oral widely used anti-viral drug. Significant protection by Oseltamivir against hearing loss is shown herein in doses equivalent to those approved for human use.

Compounds are revealed to protect against hair cell apoptosis. Compounds are identified as acting against hair cell loss in animals by the models and data presented. Models reveal properties necessary for an otoprotective compound such as high efficacy against hair cell loss, relatively low toxicity. Compounds are revealed to have high efficacy and high affinity in mouse models used to demonstrate protection against hair cell loss. Mouse models involving HEI-OC1 have shown effective in validating therapeutic uses of compounds against hearing loss due to Cisplatin, noise, antibiotics, and aging. Teitz et al, J. Exp. Med, 2; 215(4):1187-1203 (2018). Compounds are revealed to protect against the loss of functional hearing cells even when administered post-ototoxic insult. Data derived utilizing adult mice as experimental models reveals hearing cell protection is shown to be achieved after normal generation of hearing cells has ceased in mammals. Mouse models involving adults have shown effective in validating therapeutic uses of compounds against hearing loss. Rai et al., Int J Mol Sci. 23(1):66 (2022).

The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration. Compounds can be synthesized by a variety of methods known in the art.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans, Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, PA 1990.

In various aspects, the disclosed pharmaceutical compositions include the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds. The pharmaceutical carrier employed can be, for example, a solid, liquid, or gas.

The pharmaceutical compositions of the present invention include the compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability.

In various aspects, the compounds of this invention can be used in combination with one or more other drugs, in the form of a kit, to prevention, control, amelioration, or reduction of risk of hearing impairments, when the other drugs can have been known to impair hearing such as an antibiotic. Certain antibiotics, especially aminoglycosides (such as gentamicin, streptomycin, and neomycin). Hearing-related side effects from these antibiotics are most common in people who have kidney disease or who already have ear or hearing problems.

Figure 1A:
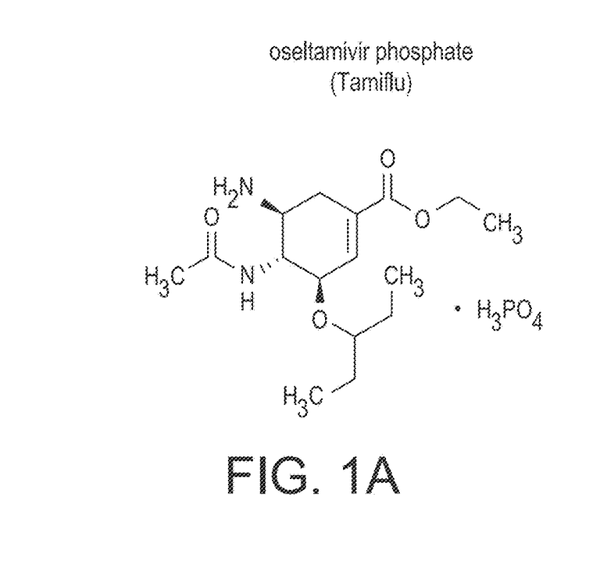
FIG. 1A shows the chemical structure of Oseltamivir
Figure 1B:
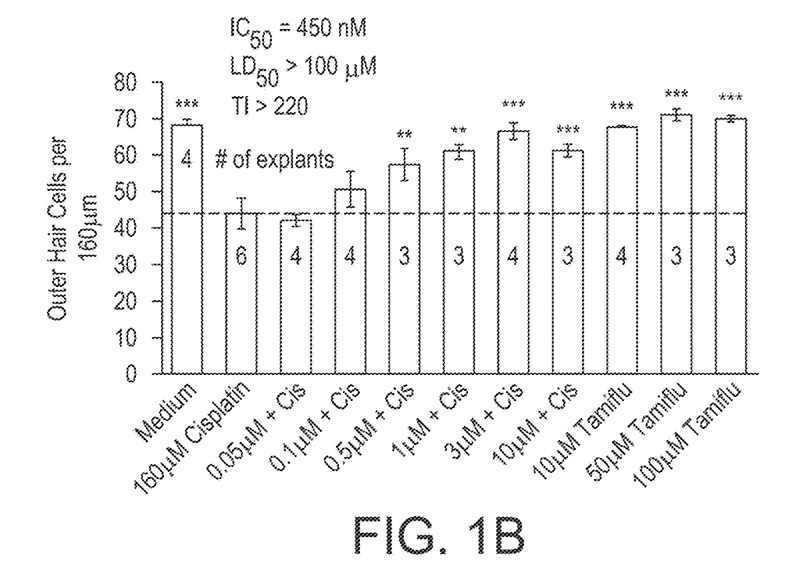
FIG. 1B shows the dose-response of Oseltamivir in P3 FVB mouse cochlear explants treated with or without cisplatin
Figure 1C:
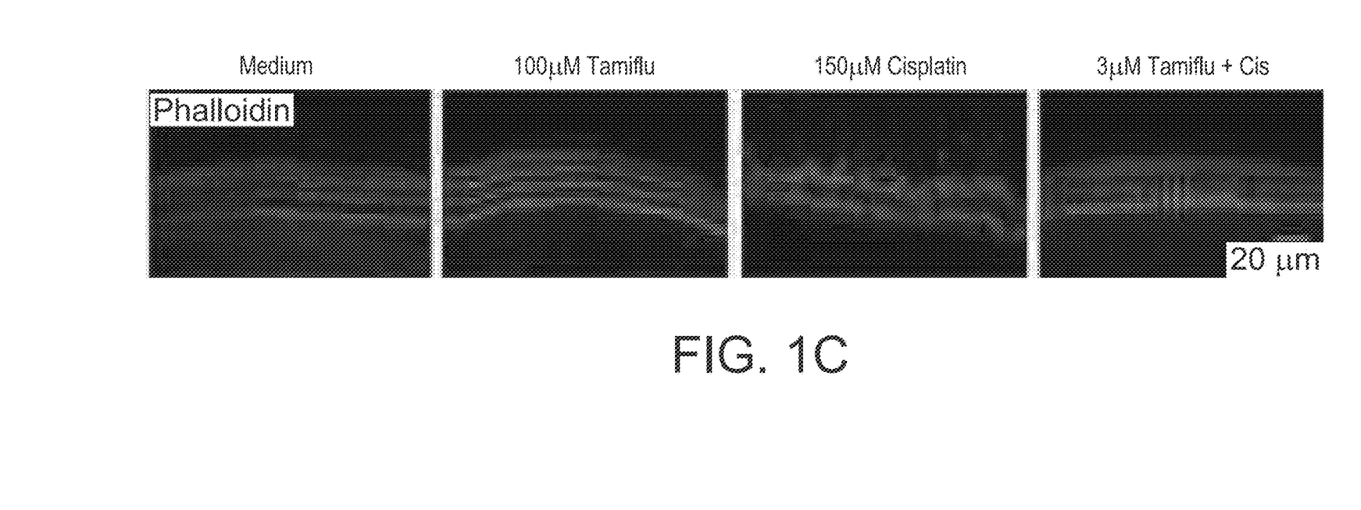
FIG. 1C shows confocal images of phalloidin-stained whole-mount middle turn cochlear.

Now referring to FIGS. 1A-C, the data shows that Oseltamivir attenuates Cisplatin-induced hearing loss in FVB/NJ mice. Now referring to FIG. 1A, a representation of the chemical structure of Oseltamivir phosphate is shown. Now referring to FIG. 1B, medium alone (Labeled medium), cisplatin alone (Labeled 150 μM Cisplatin), Oseltamivir alone at doses of 10 μM, 60 μM, 100 μM (Labeled by μM dose of Oseltamivir; doses from left to right), or Oseltamivir added 1 h before cisplatin (150 μM) at Oseltamivir doses of 0.05 μM, 0.1 μM, 0.5 μM, 1 μM, 3 μM, and 10 μM to P3 FVB cochlear explants treated for 24 h (Labeled by μM dose of test compound+Cis; doses listed left to right). The explants were treated for 24 hours. Numbers inside each bar indicate number of explants counted per treatment, where between 3 to 6 explants were counted. Percent protection for compound at the tested dosages were then plotted to show dose response curves, and $IC_{50}$ were calculated. Oseltamivir was calculated to have an $IC_{50}$ of 450 nM and therapeutic index larger than 220 μM, with an $LD_{50}$>100 μM. Oseltamivir protected from cisplatin-induced hair cell death in mouse P3 cochlear explants at concentrations of between 0.1 μM and 10 μM.

Now referring to FIG. 1C, four images representing medium alone, 100 μM of Oseltamivir alone, 150 μM of Cisplatin alone, and 3 μM Oseltamivir and Cisplatin (described from left to right). Bar in bottom right corner indicates scale of image, representing 20 μm distance. Immunofluorescent images of cochlea stained with phalloidin (red) at the middle turn region shows protection of against cisplatin induced hair cell loss when treated with Oseltamivir.

Experimental procedures for the images shown in FIG. 1C are as follows: Mice were approved by the Institutional Animal Care and Use Committee (IACUC) at the Creighton University. Inner ears were collected from the post-natal day 3 (P3) FVB mice and transferred onto a filter (Millicell, PICM03050; Millipore) soaked in culturing medium. The filter was placed in 6-well culture plates with 1.2 mL medium outside the filter. The culturing medium is DMEM (10565-018; gibco) with 1% FBS (16000-044; gibco), 500 μL ampicillin (A5354; Sigma), 100 μL N-2 supplement (17502-048, gibco) and 100 μL B-27 supplement (17504-044, gibco). Cells may be maintained in culture with the aid of Matrigel as previously described in Kelley and Driver, Curr. Protoc. Neurosci. Ch.(4); Unit(4); 34.1-10 (2010). After cells had been in culture for 1 d, growth medium DMEM (12430-054; GIB CO Life Technologies, with 1%

FBS [16000-044; GIB CO Life Technologies]) with or without test compounds may be added for preincubation for 1 hr. at 370 in 5% Co2, and may be followed by incubation with Cisplatin (479306; Sigma-Aldrich) with or without the test compound in growth medium for 24 hr. at 37° C. Cochlea may be fixed in 4% PFA and stained for actin with Alex Fluor 568 phalloidin to determine the viability of the HCs. Cochlea may also be stained by DAPI, FM1-43 dye uptake, and immunohistochemical staining for known HG markers (including parvalbumin and myosin 7a. Cochlea may be imaged by confocal microscopy, Two 160-μm regions from middle turns may be photographed, and the number of intact HCs can be counted. All the cochleae images were taken with Zeiss 700 confocal microscopy. Number of outer hair cells per 160 μm of middle turn regions of the cochlea were counted by phalloidin staining, mean±SEM, P=<0.01, *<0.001 compared to cisplatin alone by unpaired one-way ANOVA with Bonferroni post hoc test. Cisplatin doses of 50-150 μM consistently show the loss of about ~40% outer hair cells within 24 hr., based on dose responses of Cisplatin at 50, 100, 150, and 200 μM. Teitz et al., J. Exp. Med. 215(4):1187-1203 (2018).

Figure 2A:
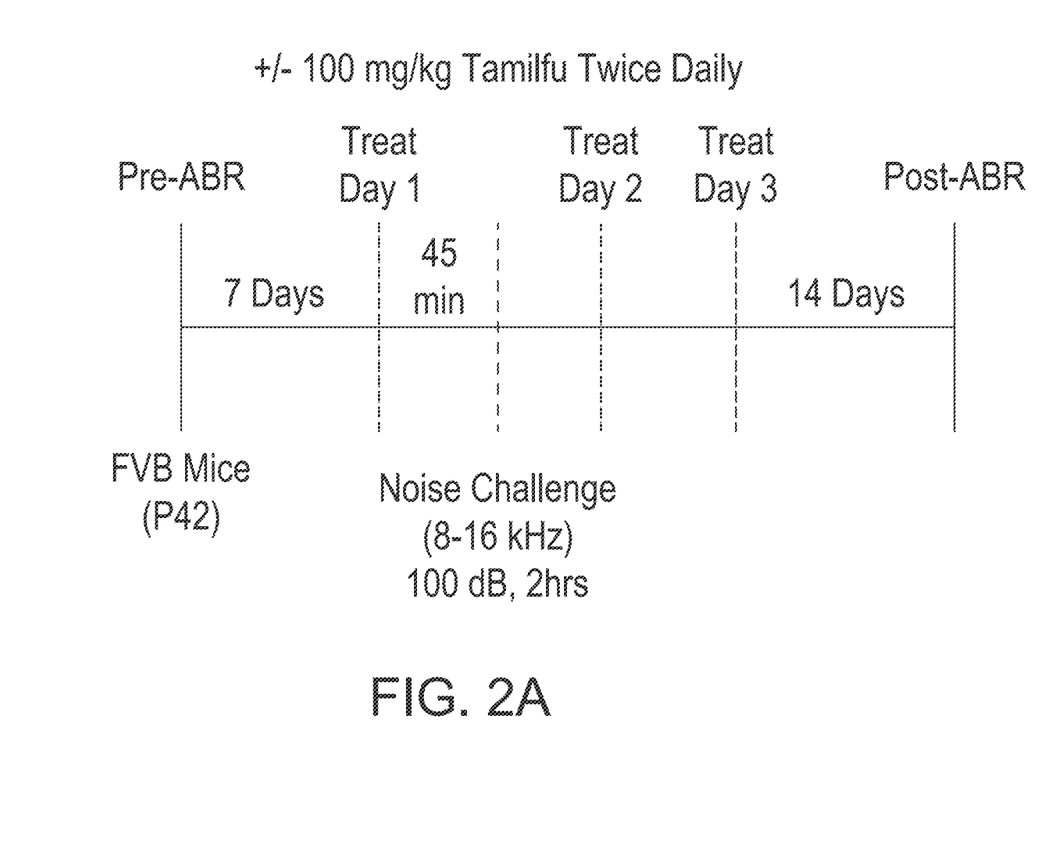
FIG. 2A shows the schedule of administration of Oseltamivir
Figure 2B:
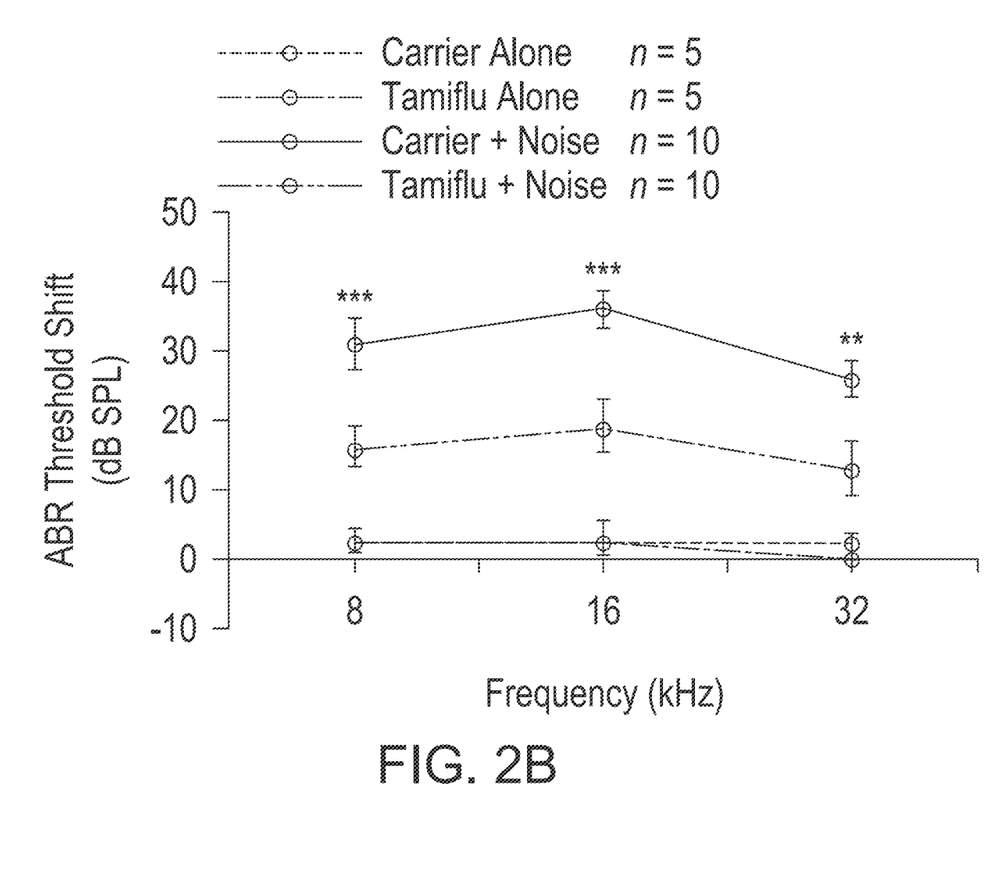
FIG. 2B shows auditory Brainstem Response threshold shifts recorded 14 days after 100 dB, 8-16 kHz octave band noise.

Now referring to FIGS. 2A-B shows pre-treatment with Oseltamivir before noise exposure preserves normal hair cell function in adult mice. Now referring to FIG. 2A, adult P42 FVB mice began treatment with Oseltamivir administered oral gavage at 100 mg/kg body weight twice daily for three days once 45 minutes before exposure and then for two days after noise exposure. Now referring to FIG. 2B, auditory brainstem response (ABR) were recorded 14 days after noise exposure of 100 dB, 8-16 kHz octave band, for two hours. Significant protection against hearing loss was observed when animals were treated with Oseltamivir at recorded frequencies compared to the control group exposed to noise. n equals the number of mice per recording. Control is shown as carrier. Statistical analysis was done with repeated measures ANOVA between groups. Mean±SEM, P=<0.01, *<0.001, compared to noise alone by two-way ANOVA with Bonferroni post-hoc test. Significant protection of 24-28 dB was observed with auditory brainstem response measurements when the drug was administered orally 45 minutes before noise exposure.

The experimental procedures for the data shown in FIGS. 2A-B are as follows: Animals were anesthetized with avertin. Subcutaneous needle electrodes were inserted behind the pinna (inverting), vertex of the skull (non-inverting) and base of the tail (ground). Tone bursts of 5 ms duration with 0.5 ms cosine-squared envelopes delivered at a rate of 21 stimuli per second with alternating polarity were generated using BioSigRZ software and RZ6 multi I/O processor system (Tucker-Davis Technologies, FL). Stimuli were presented as open field via a speaker (MF1: TDT, FL) placed 10 cm in front of the pinna of the animal. Evoked responses were amplified (20×), bandpass filtered (300-3,000 Hz) and average of 512 responses of 10 ms duration was recorded. Stimulus intensity was decreased in 5 dB increments, starting from 100 dB SPL to 0 dB SPL. Thresholds at 4, 5.6, 8, 16, 22.6, 32, 45.2, and 64 kHz were identified by visual inspection from stacked waveforms as the lowest level at which reproducible response could be identified. Before the start of every session, stimulus presenting speaker (MF1) was calibrated with a ¼" microphone (PCB-378C10; PCB Piezotronics, NY) that was also placed 10 cm in front of the speaker. Similar experiments have been previously described in Rai V. et al., Sci Rep. 2020 Sep. 16; 10(1): 15167.

FIGS. 3A-F shows treatment with Oseltamivir 24 hours after noise exposure preserves normal hair cell function in adult mice. Now referring to FIG. 3A, adult P42 FVB mice began treatment with Oseltamivir administered oral gavage at 100 mg/kg body weight twice daily for three days beginning 24 hours following noise exposure of 100 dB, 8-16 kHz octave band, for two hours. Now referring to FIG. 3B, auditory brainstem response (ABR) were recorded 14 days after noise exposure of 100 dB, 8-16 kHz octave band, for two hours. Significant protection against hearing loss was observed when animals were treated with Oseltamivir at recorded frequencies compared to the control group exposed to noise, n equals the number of mice per recording. Control is shown as carrier. Statistical analysis was done with repeated measures ANOVA between groups. Mean±SEM, P=<0.01, *<0.001, compared to noise alone by two-way ANOVA with Bonferroni post-hoc test. Oseltamivir's protection against hearing loss when administered post noise exposure suggests Oseltamivir offers a novel function in hearing therapy, Oseltamivir protected adult mice by oral delivery against permanent noise-induced hearing loss.

Figure 3A:
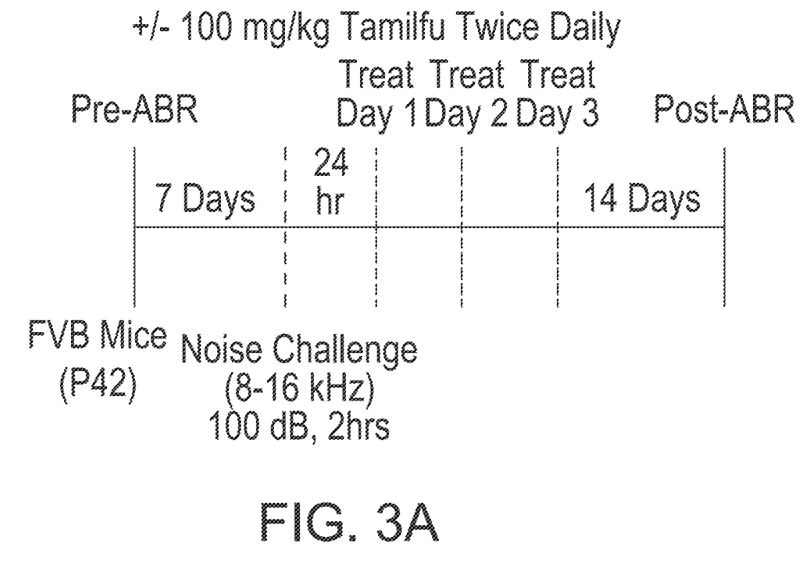
FIG. 3A shows the schedule of administration of Oseltamivir.
Figure 3B:
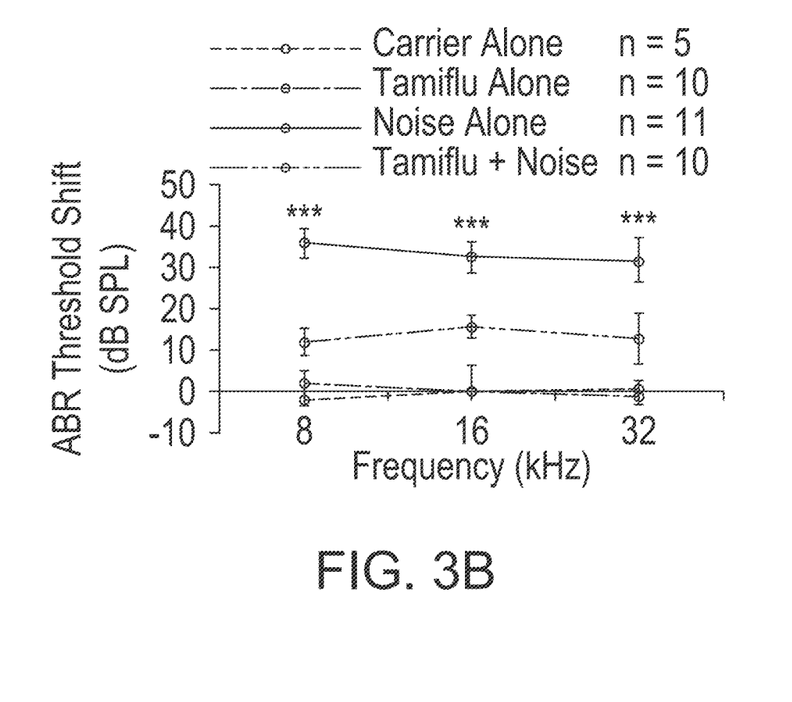
FIG. 3B shows auditory Brainstem Response threshold shifts recorded 14 days after 100 dB, 8-16 kHz octave band noise.
Figure 3C:
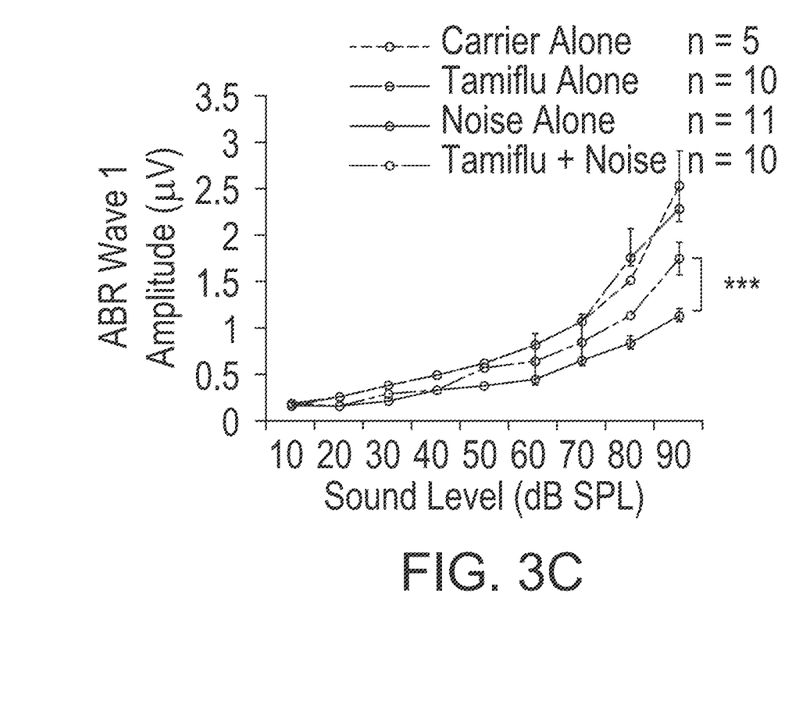
FIG. 3C shows Amplitudes of auditory Brainstem Response wave 1 from record auditory Brainstem Response threshold shifts.

Now referring to FIG. 3O, amplitudes of auditory Brainstem Response wave 1 from auditory brainstem response recording of FIG. 3A. The auditory Brainstem Response wave-1 amplitude represents the summed activity of the cochlear nerve. Mean wave-1 amplitudes was measured in the control and Oseltamivir-treated mice before and after noise exposure. Amplitudes from the 90 dB SPL stimuli were compared between groups using a two-factor ANOVA (group× frequency), and difference was detected between the noise alone group to Oseltamivir plus noise. at 14 days post-noise exposure. The noises exposed-Oseltamivir treated group had higher amplitudes compared to the noise exposure only group at 16 kHz at the 90 dB SPL noise level.

Figure 3D:
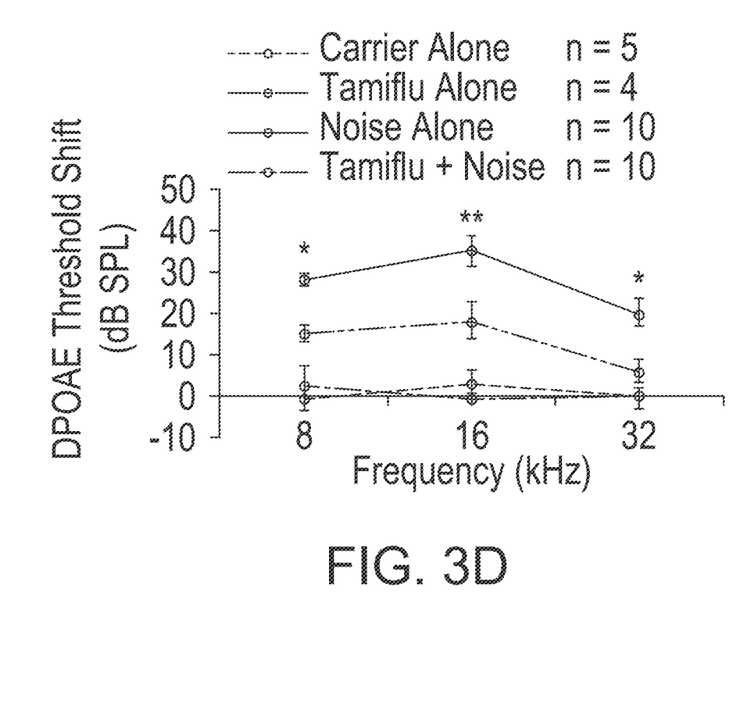
FIG. 3D shows DPOAE threshold shifts recorded 14 days after 100 dB, 8-16 kHz octave band noise.

Now referring to FIG. 3D, Distortion Product Otoacoustic Emissions (DPOAE) threshold shifts were measured in adult FVB mice 14 days after noise exposure of 100 dB, 8-16 kHz octave band, for two hours. DPOAE audiograms provide a direct indicator of cochlear sensitivity at the level of the OHC. Significant protection against hearing loss was observed when animals were treated with Oseltamivir at recorded frequencies compared to the control group exposed to noise. n equals the number of mice per recording. Control is shown as carrier. Statistical analysis was done with repeated measures ANOVA between groups. Mean±SEM, P=<0.01, *<0.001, compared to noise alone by two-way ANOVA with Bonferroni post-hoc test. Significant protection between 20-28 dB was observed with auditory Brainstem Response and DPOAE measurements when the drug was administered orally 45 minutes before noise exposure and when administered 24 hours after noise exposure to mice for three consecutive days.

Figure 3E:
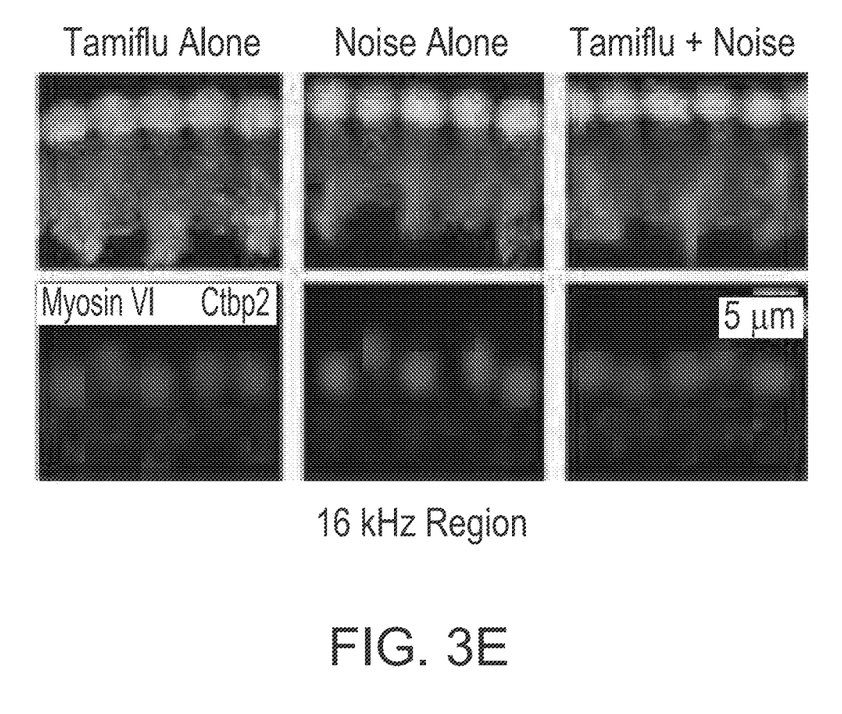
FIG. 3E shows Ctbp2 puncta (red) and myosin VI (green) stained confocal images of inner hair cells in whole-mouse mouse cochlea at the 16 kHz cochlear region.

Now referring to FIG. 3E, Oseltamivir restores functional integrity of CtBP2 gene within the cochleae of adult mice. Cochleae were co-stained for synaptic ribbon scaffolding protein, CtBP2, to measure loss of synaptic ribbon integrity in inner hair cells at the 16 kHz region. Treatment with Oseltamivir partially restores loss of the CtBP2-puncta in the mice cochleae compared to mice exposed with noise alone. Oseltamivir restores the functional integrity of ear cells in the subject in need thereof from damage caused by noise.

Figure 3F:
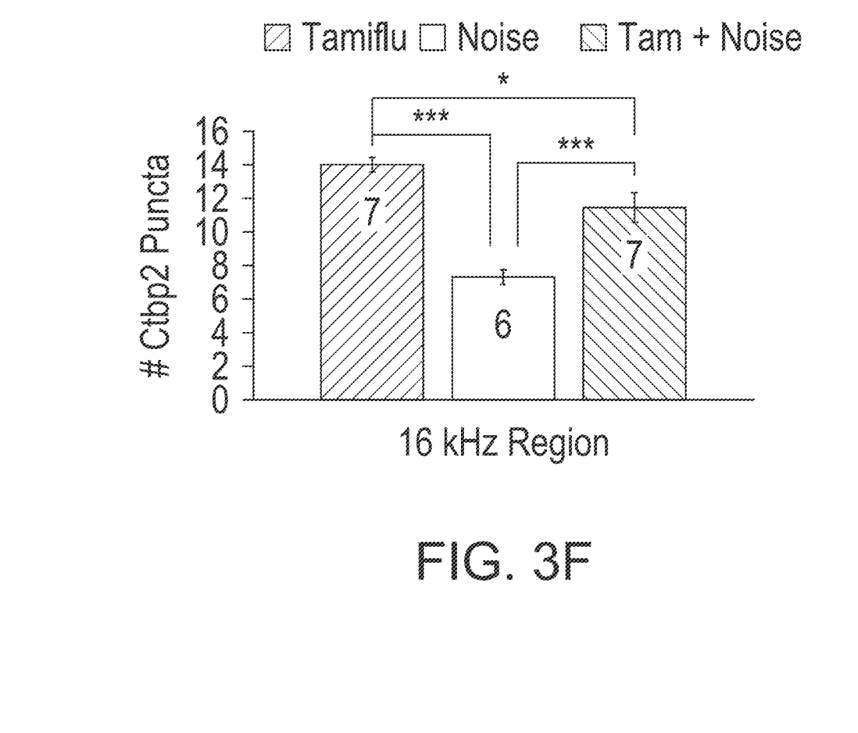
FIG. 3F shows the number of Ctbp2 puncta per inner hair cell at the 16 kHz cochlear region.

Now referring to FIG. 3F, Oseltamivir administered post-noise exposure is shown to increase number of CtBP2 puncta. Number of CtBP2 puncta per IHC at the 16 kHz cochlear region were counted, data shown as mean±SEM, P=<0.01, *<0.001 by one-way ANOVA with Bonferroni post-hoc test, n=6-7 cochleae. An average of 4 CtBP2 puncta per IHC are restored compared to group exposed to noise without Oseltamivir treatment.

Experimental procedure for distortion product otoacoustic emissions (DPOAE) measurements, primary tones were set to generate 2f1-f2 distortion products at frequencies between 1 and 50 kHz, DPOAEs were measured for levels of f1 ranging from 10 to 80 dB SPL, with the levels of the f2 tone set 10 dB below that of the f1 tone. Similar experiments are described in Lukashkina A. V. et al., Scientific reports, July 12; 7(1), 5185. (2017). Similar Ctpb2/MyosinVI experiments are described in Liu Z et al., PLoS One. Feb. 20, 2014; 9(2):e89377 (2014).

Figure 4A:
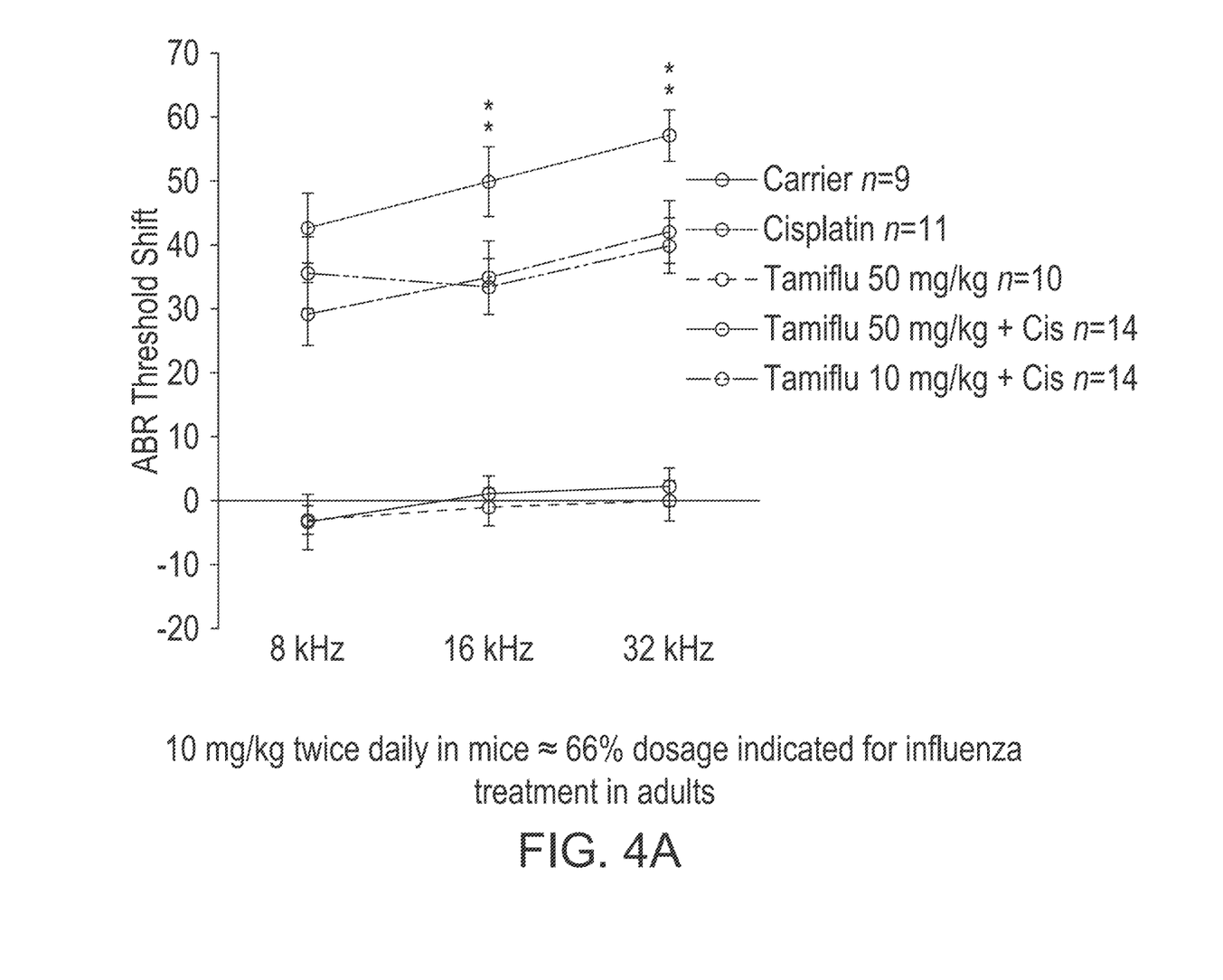
FIG. 4A shows auditory Brainstem Response threshold shift following multi-cycle cisplatin treatment recorded at 8-32 kHz.
Figure 4B:
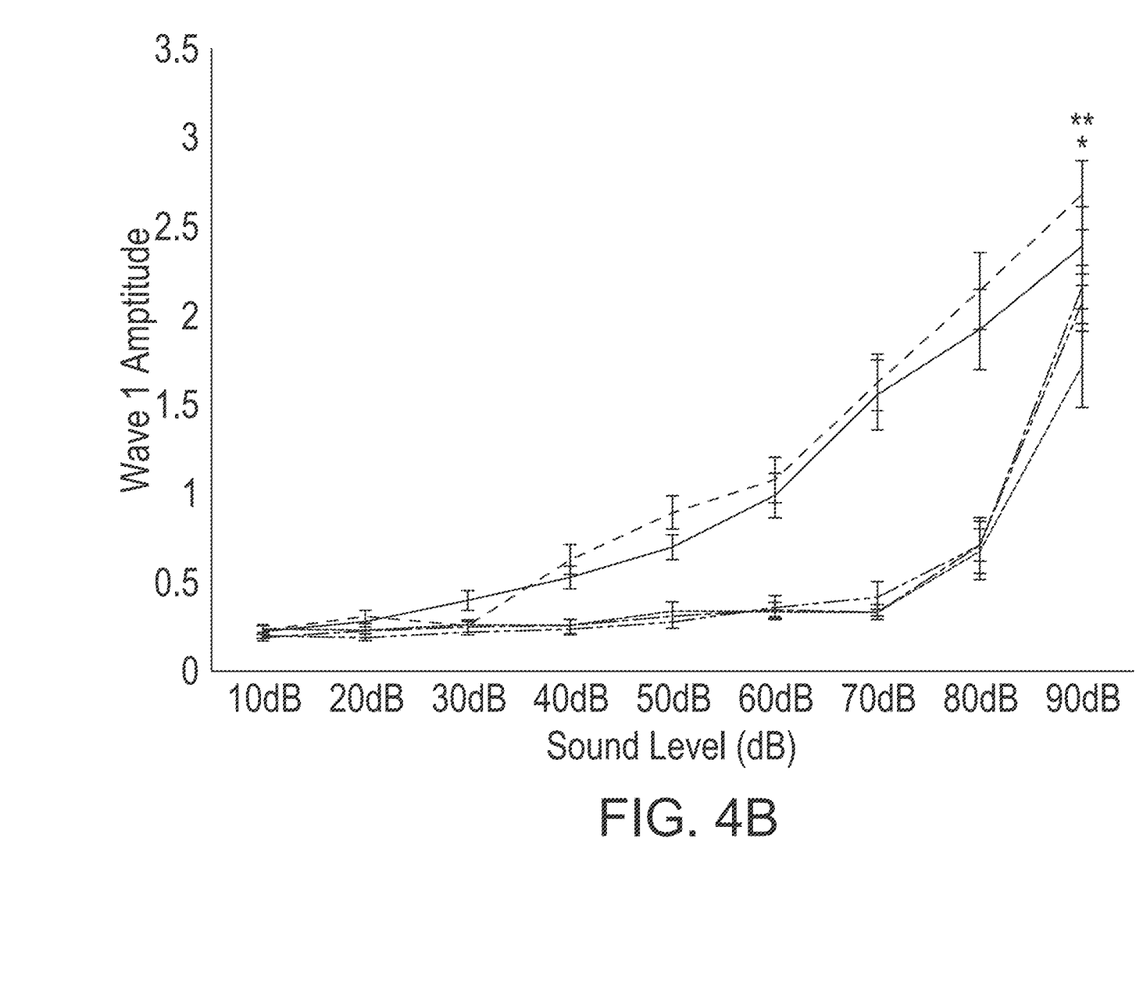
FIG. 4B shows Wave-1 amplitude recordings following multi-cycle cisplatin treatment recorded at 16 kHz from 10-90 dB.
Figure 4C:
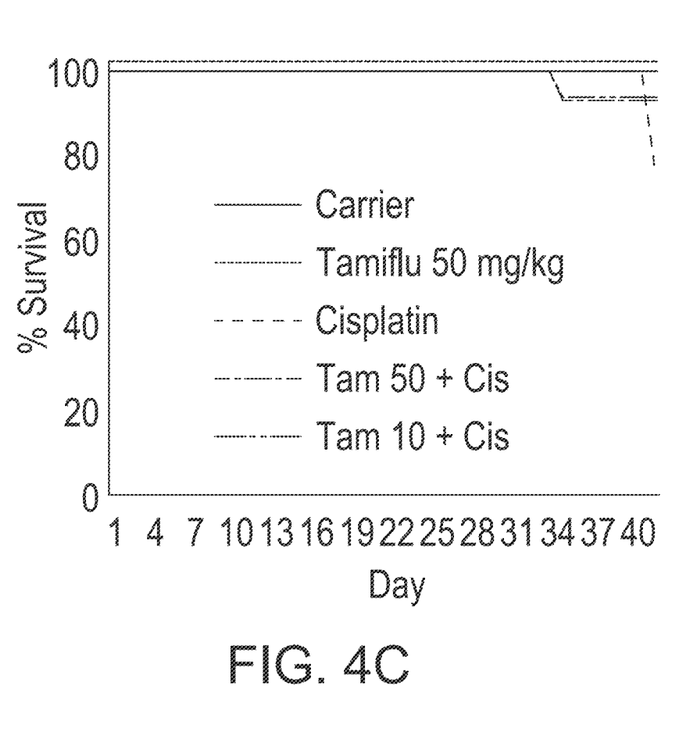
FIG. 4C shows survival of adult mice with out without treatment.

Now referring to FIGS. 4A-C, the data shows that Oseltamivir protects against cisplatin-induced hearing loss in adult 12 weeks old CBA/CaJ mice in a multi-dose cisplatin regimen—3 mg/kg body weight cisplatin given in 3 cycles. Each cycle consists of a 4-day periods of once-daily 3 mg/kg cisplatin IP injection coupled with 5-day twice-daily 50 mg/kg or 10 mg/kg Oseltamivir treatment by oral gavage beginning 45 min prior to cisplatin injection and followed by 9 days of recovery, Now referring to FIG. 4A, mice exposed to cisplatin with treatment showed lower auditory brainstem response threshold shift recordings at 8, 16, and 32 kHz at doses of 10 and 50 mg/kg of Oseltamivir. N=number of cochleae.

Now referring to FIG. 4B, mice exposed to multi-dose cisplatin treatments show reduced reduction in wave 1 amplitude 16 kHz recording form 30-90 dB SPL, and Oseltamivir treatment at the dose of 50 mg/kg increased the 16-kHz wave-1 amplitude at 90 SPL.

Now referring to FIG. 4C, Oseltamivir (10 mg/kg and 50 mg/kg doses) increased the percent of total mice surviving 40 days after beginning of cisplatin exposure. Auditory Brainstem Response threshold shifts recorded as previously described. Similar wave-1 amplitude recordings have been described Hazlitt J et al., Med. Chem. 61, 7700-7709 (2018); Teitz et al., J. Exp. Med. 215, 1187-1203 (2018).

Figure 5A:
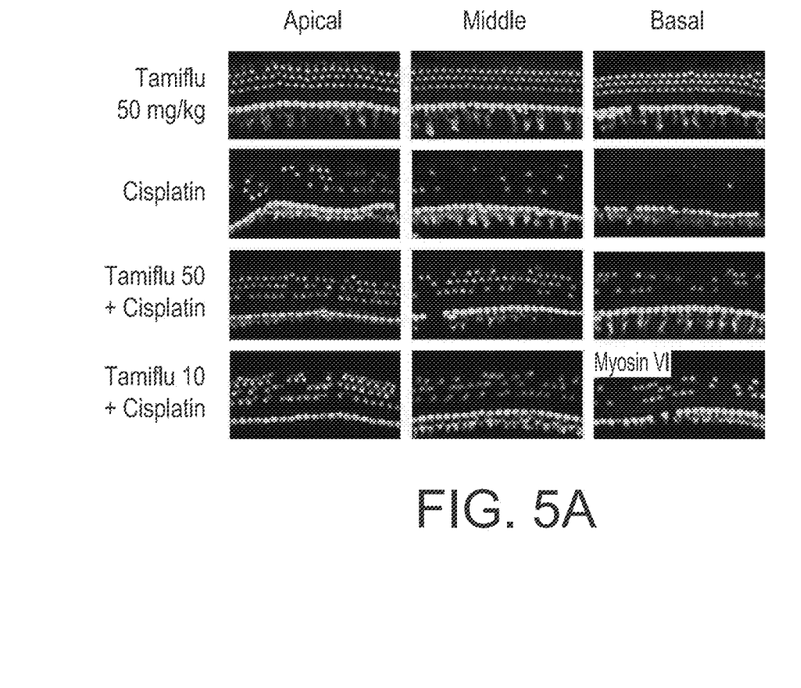
FIG. 5A shows confocal images of myosin VI stained basal, middle, apical turn cochlear regions.
Figure 5B:
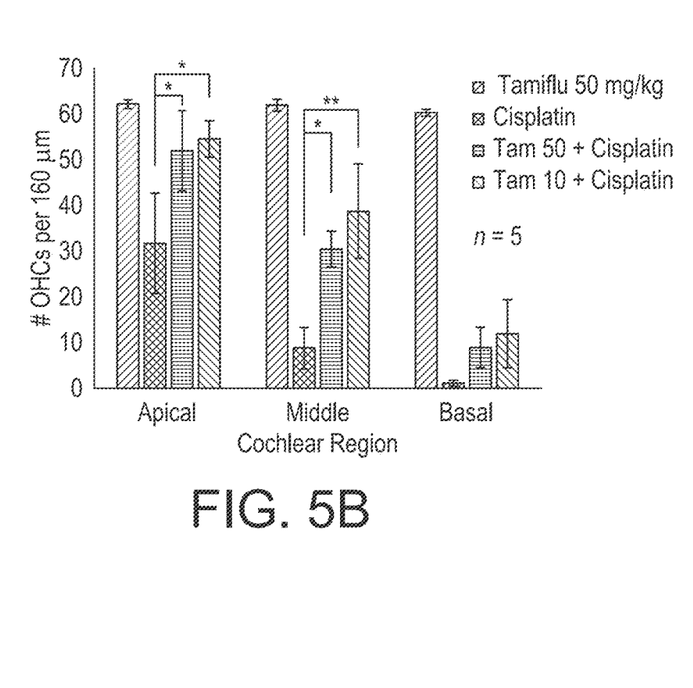
FIG. 5B shows the count of outer hair cells per 160 µm for cochlear regions.

Now referring to FIGS. 5A-B, in cochlear regions of cisplatin exposed adult mice treated with the multi-dose cisplatin regimen (3 mg/kg body weight cisplatin given in 3 cycles of 4 consecutive days to CBA/CaJ mice) stained with Myosin VI Oseltamivir treated mice preserved outer hair cells in all regions. Now referring to FIG. 5A, confocal images of myosin-VI stained basal, middle, apical turn cochlear regions show outer hair cells of mice exposed to treatment of 50 mg/kg Oseltamivir alone or exposed to cisplatin with or without treatment of 10 or 50 mg/kg Oseltamivir. Now referring to FIG. 5B, count of outer hair cells per 160 µm for cochlear regions. Mean±SEM, P=*<0.05, **<0.01, compared to noise alone by two-way ANOVA with Bonferroni post-hoc test. N=5 cochleae counted per bar. Similar Myosin VI experiments are described in Liu Z et al., PLoS One. Feb. 20, 2014; 9(2): e89377 (2014).

FIGS. 6A-D illustrates Oseltamivir's treatment 24 hours after noise exposure protects adult mice against noise-induced hearing loss. FIG. BA shows recordings of auditory brainstem response threshold shift following 100 mg/kg Oseltamivir (TMF), 50 mg/kg Oseltamivir and 10 mg/kg Oseltamivir with or without noise recorded at 8, 16, 32 kHz; the difference in dB SPL recorded at each recording; and calculation of percent difference auditory Brainstem Response threshold shift recorded.

Figure 6A:
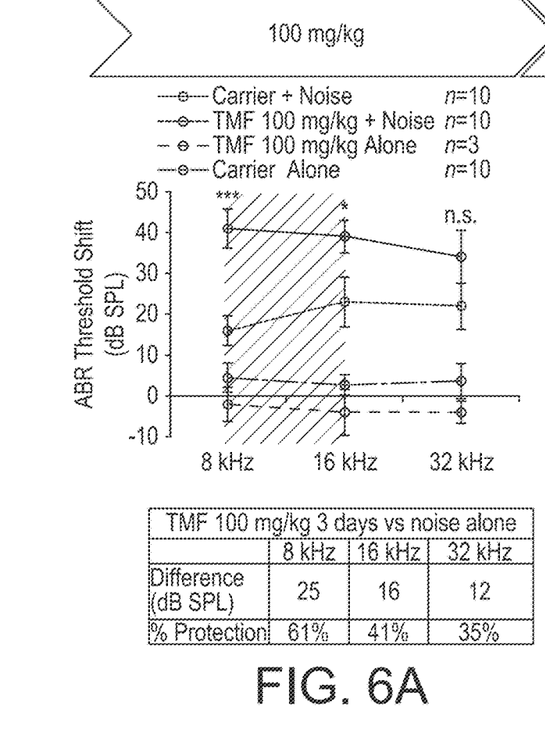
FIG. 6A shows recordings of auditory Brainstem Response threshold shift following 100 mg/kg Oseltamivir (TMF) with or without noise recorded at 8, 16, 32 kHz; the difference in dB SPL recorded at each recording; and calculation of percent difference auditory Brainstem Response threshold shift recorded.
Figure 6B:
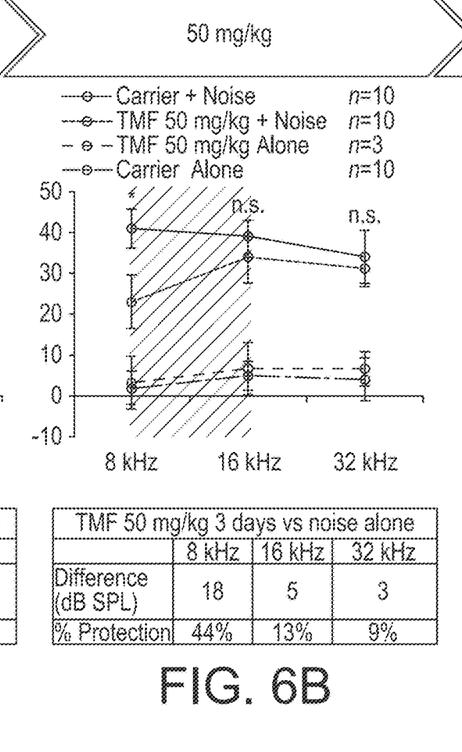
FIG. 6B shows recordings of auditory Brainstem Response threshold shift following 50 mg/kg Oseltamivir (TMF) with or without noise recorded at 8, 16, 32 kHz; the difference in dB SPL recorded at each recording; and calculation of percent difference auditory Brainstem Response threshold shift recorded.

FIG. 6A shows recordings of auditory brainstem response threshold shift following 50 mg/kg Oseltamivir (TMF) with or without noise recorded at 8, 16, 32 kHz; the difference in dB SPL recorded at each recording; and calculation of percent difference auditory brainstem response threshold shift recorded.

Figure 6C:
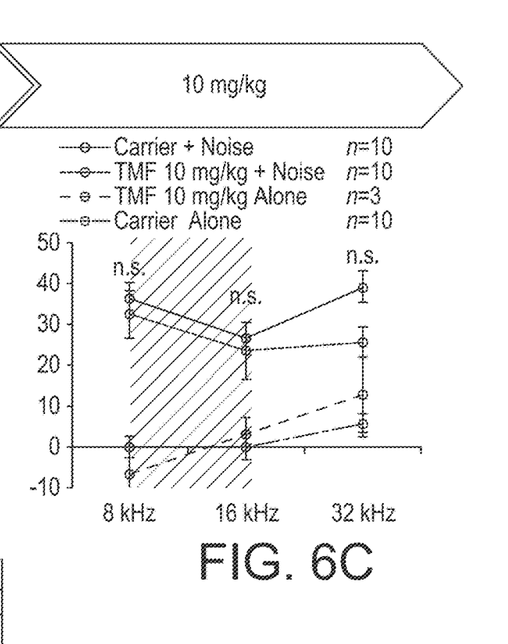
FIG. 6C shows recordings of auditory Brainstem Response threshold shift following 10 mg/kg Oseltamivir (TMF) with or without noise recorded at 8, 16, 32 kHz.

FIG. 6C shows recordings of auditory brainstem response threshold shift following 10 mg/kg Oseltamivir (TMF) with or without noise recorded at 8, 16, 32 kHz.

Figure 6D:
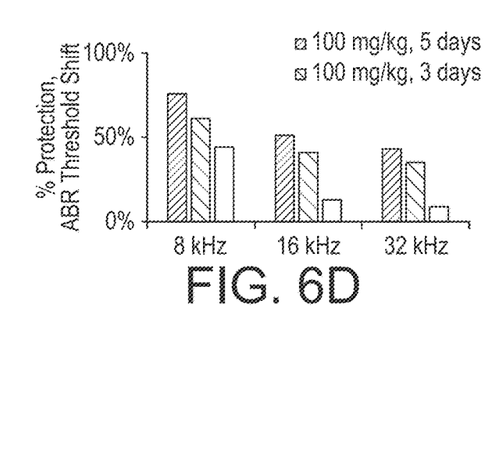
FIG. 6D shows percentage of protection against noise induced-hair cell loss when treatment of Oseltamivir is administered to mice at 100 mg/kg for 3 days, 5 days and 100 mg/kg for 3 days.

FIG. 6AD shows percentage of protection against noise induced-hair cell loss when treatment of Oseltamivir is administered to mice at 100 mg/kg for 3 days, 5 days and 100 mg/kg for 3 days. Auditory brainstem response experiments are described previously.

All publications, patents and patent applications mentioned in this specification are herein incorporated by reference to the same extent as if each individual publication, patent, or patent application was specifically and individually indicated to be incorporated by reference.

While the invention has been described with reference to details of the illustrated embodiments, these details are not intended to limit the scope of the invention as defined in the appended claims. The embodiment of the invention in which exclusive property or privilege is claimed is defined as follows:

What is claimed:

1. A method protect ear cells from death caused by acoustic overexposure comprising:
administering to a subject in need thereof an effective amount of a pharmaceutical composition containing a therapeutically active agent to preserve hair cell function wherein the therapeutically active agent is: oseltamivir wherein the composition is administered prior to or following acoustic overexposure.

2. A method to protect ear cells from death caused by cisplatin treatment comprising administering to a subject in need thereof an effective amount of a pharmaceutical composition containing a therapeutically active agent to reduce hearing loss, wherein the therapeutically active agent is oseltamivir wherein the composition is administered prior to cisplatin treatment.

3. A method to protect against hair cell apoptosis caused by cisplatin treatment comprising: administering to a subject in need thereof an effective amount of a pharmaceutical composition containing a therapeutically active agent to protect ear cells from death, wherein the therapeutically active agent is oseltamivir, wherein oseltamivir is administered in the dosage range of between 10 mg/kg and 100 mg/kg in a mouse subject or an equivalent dosage in a human subject wherein the composition is administered prior to cisplatin treatment.

4. A method to protect ear cells from death caused by acoustic overexposure comprising: administering to a subject in need thereof an effective amount of a pharmaceutical composition containing a therapeutically active agent to preserve hair cell function wherein the therapeutically active agent is oseltamivir, wherein oseltamivir is administered in the dosage range of between 10 mg/kg and 100 mg/kg in a mouse subject or an equivalent dosage in a human subject and wherein the composition is administered prior to or following acoustic overexposure.

* * * * *